(12) United States Patent
Li

(10) Patent No.: US 10,864,000 B2
(45) Date of Patent: Dec. 15, 2020

(54) MEMORY ELASTIC WIRE SLEEVE FOR PEELING MAXILLARY SINUS MEMBRANE

(71) Applicant: Yanfeng Li, Beijing (CN)

(72) Inventor: Yanfeng Li, Beijing (CN)

(73) Assignee: Yanfeng Li, Beijing (CN)

( * ) Notice: Subject to any disclaimer, the term of this patent is extended or adjusted under 35 U.S.C. 154(b) by 263 days.

(21) Appl. No.: 15/755,992

(22) PCT Filed: Sep. 17, 2015

(86) PCT No.: PCT/CN2015/089842
§ 371 (c)(1),
(2) Date: Feb. 27, 2018

(87) PCT Pub. No.: WO2017/035872
PCT Pub. Date: Mar. 9, 2017

(65) Prior Publication Data
US 2018/0193116 A1 Jul. 12, 2018

(30) Foreign Application Priority Data

Aug. 31, 2015 (CN) .......................... 2015 1 0548208
Aug. 31, 2015 (CN) ...................... 2015 2 0669139 U

(51) Int. Cl.
*A61B 17/24* (2006.01)
*A61B 17/3211* (2006.01)
(Continued)

(52) U.S. Cl.
CPC .......... *A61B 17/24* (2013.01); *A61B 17/3211* (2013.01); *A61C 8/0006* (2013.01); *A61C 8/0092* (2013.01); *A61C 2201/007* (2013.01)

(58) Field of Classification Search
CPC .............. A61B 17/24; A61B 2017/242; A61B 2017/246; A61B 17/3211; A61B 2017/248; A61B 2017/32113; A61C 8/0092

See application file for complete search history.

(56) References Cited

U.S. PATENT DOCUMENTS

2008/0161846 A1  7/2008 Yamada
2008/0161934 A1  7/2008 Yamada
(Continued)

FOREIGN PATENT DOCUMENTS

CN     201879783 U   6/2011
CN     104605915 A   5/2015
(Continued)

OTHER PUBLICATIONS

International Search Report for PCT/CN2015/089842 (PCT/ISA/210) dated Jun. 8, 2016.

*Primary Examiner* — Sarah A Simpson
(74) *Attorney, Agent, or Firm* — Birch, Stewart, Kolasch & Birch, LLP

(57) ABSTRACT

A memory elastic wire sleeve for peeling maxillary sinus mucous membrane is adapted for implant surgeries and/or bone grafting in the regions close to the maxillary sinus floor. The memory elastic wire sleeve includes a primary peeling structure and a secondary peeling structure, wherein the primary peeling structure comprises a hollow sleeve and a peeling edge located on the top of the hollow sleeve, and can peel the maxillary sinus mucous membrane preliminarily, and the second peeling structure is a memory elastic wire which can further peel the maxillary sinus mucous membrane. The memory elastic wire sleeve is simple and dainty, and can safely and effectively peel away the maxillary sinus mucous membrane within a large range.

7 Claims, 2 Drawing Sheets

(51) Int. Cl.
*A61C 8/02* (2006.01)
*A61C 8/00* (2006.01)

(56) References Cited

U.S. PATENT DOCUMENTS

| | | | |
|---|---|---|---|
| 2008/0182225 A1 | 7/2008 | Gordils Wallis | |
| 2010/0241155 A1* | 9/2010 | Chang | A61M 25/0068 606/196 |
| 2015/0039014 A1* | 2/2015 | Schaeffer | A61B 17/12104 606/199 |
| 2016/0015944 A1* | 1/2016 | Jenkins | A61M 25/09041 604/510 |
| 2018/0000499 A1* | 1/2018 | Altman | A61B 17/32002 |
| 2019/0290314 A1* | 9/2019 | Gemer | A61B 17/24 |

FOREIGN PATENT DOCUMENTS

| | | |
|---|---|---|
| CN | 203662864 U | 5/2015 |
| JP | 2006-305215 A | 11/2006 |

* cited by examiner

MEMORY ELASTIC WIRE SLEEVE FOR PEELING MAXILLARY SINUS MEMBRANE

TECHNICAL FIELD

The present invention relates to a medical appliance, particularly to a memory elastic filament cannula for stripping away maxillary sinus floor mucosa, which is applicable to implant of maxillary sinus floor mucosa and (or) bone graft.

BACKGROUND

Oral implantology is one of the fields that developed fastest in the oral medicine in recent years. It is clinically common that implant failure ratio increases due to the insufficient bone that combine with the implant when the alveolar crest in the maxillary molar area is close to the maxillary sinus floor. The maxillary molar region with insufficient vertical bone amount has once been considered as the forbidden region for dental implant.

The maxillary sinus elevation technique brings about possibility of addressing the above-mentioned problem once it is proposed.

Sinus lifting is classified into one kind of sinus lifting by windowing in sidewall, namely outside sinus lifting (Tatum O H. Maxillary and sinus implant reconstruction[J]. J Dent Clin North Am, 1986, 30(2):207-229) and the other kind of sinus lifting by accessing through alveolar crest, namely in sinus lifting (Summers R B. The osteotome technique. Part 3: Less invasive met hods in elevation of the sinus floor[J]. J Compendium of Continuous Education in Dentistry, 1994, 15:698-708.)

Sinus floor lifting by windowing in sidewall may strip away sinus floor mucosa by a large area, reducing the sinus floor mucosa's tension, may implant more bone dust to effectively increase bone height at the floor, and extends the indications of implant. However, the technique is complex and uses existing instruments for operation for a long time, and perforation likelihood increases when the stripping range increases, which makes it be limited in clinical promotion.

Sinus floor lifting by accessing through alveolar crest has advantages such as small operative wound, less postoperative complications, reduced treatment time and low cost and has been appreciated and accepted by clinical physicians. However, when the lifting amount is greater than 5 mm, and the risk of tearing sinus mucous increases significantly with common complications such as perforation of sinus mucous, formation of dead bone and maxillary sinusitis. In recent years, advanced technologies such as balloon, hydraulic pressure and piezosurgery have been applied to sinus floor lifting by accessing through alveolar crest to increase the lifting height and reduce the risk of sinus mucous perforation. However, the lifting height is limited, and it is reported by documents 2-7 mm may be lifted (Lixn Qiu, Xiulian Hu, Bo Chen et al. Clinical observation of implant repairing 122 missing teeth by sinus floor punch lifting [J]. Chinese Journal of Stomatology, 2006, 41:136-139; Nedir R, Bischof M, Vazquez L, et al. Osteotome sinus floor elevation without grafting material: a 1-year prospective pilot study with ITI implants[J]. J Clin. Oral Impl. Res, 2006, 17: 679-686; Winter A A, Pollack A S, Odrich R B. Sinus/alveolar crest tenting (SACT): a new technique for implant placement in atrophic maxillary ridges without bone grafts or membranes [J]. The International Journal of Periodontics & Restorative Dentistry, 2003, 23: 557-565). The main reason is that the inside lifting can only strip away small range of mucous membrane by appliance although it causes small operative wound.

The present invention creatively provides a medical appliance in view of the problems with stripping away sinus floor mucous by appliance, which can be used in stripping away large area of sinus floor mucous by accessing through alveolar crest or by windowing in sidewall, safe and effective, having promising clinical application value.

SUMMARY

The object of the present invention is to provide a cannula with memory elastic filament for stripping away sinus mucous, which includes a primary stripping structure and a secondary stripping structure, said primary stripping structure consisting of a hollow cannula and a stripping edge at the top of the hollow cannula, said secondary stripping structure adopts an elastic filament, characterized in that said elastic filament has ultra-elasticity and/or memory, the elastic filament passes into the hollow cannula from its bottom, and the stripping edge controls the elastic filament to extend forward and downward from the end of the hollow cannula.

Furthermore, the part of the elastic filament that extend beyond the hollow cannula is referred to as stripping filament that is variable in terms of size, extension direction and shape.

Furthermore, the elastic filament is bent into double strands and the part of the elastic filament that extends beyond the hollow cannula is referred to as stripping filament (8).

Furthermore, the elastic filament is machined to have a shape suitable for stripping away the maxillary sinus floor mucous and the elastic filament is penetrated into the hollow cannula during assemble of said cannula with memory elastic filament.

Preferably, said shape suitable for stripping away the maxillary sinus floor mucous is an arc or cone.

Furthermore, the stripping filament is of an irregular circle shape.

Furthermore, the stripping filament expands so as to be hidden in the stripping edge but can not continue retracting into the hollow cannula.

Furthermore, the stripping edge is of an arc shape and/or an end of the hollow cannula has a holding portion; and/or an end of the elastic filament has a stop plug; and/or the hollow cannula is marked with scale; and/or the elastic filament is marked with scale.

Preferably, the distance between scale marks is preferably 0.5-1 mm.

Preferably, the holding portion is sized to facilitate holding, and more preferably, the holding end has a diameter greater than 7 mm.

When the elastic filament is bent into double strands, an end of each strand has a stop plug, wherein when the stop plug is pushed or pulled, the elastic filament expands or shrinks and the stripping filament changes its size; when the stop plug is rotated, the elastic filament is rotated, and the stripping filament reverses; when the stop plugs remain in different motions, the stripping filament changes it shape; and when one of the stop plugs keeps stationary and the other moves, the stripping filament changes its shape.

Preferably, the stop plug may move along the elastic filament and be secured at a specified position.

More preferably, at the beginning of stripping away the maxillary sinus mucous, when only the primary stripping structure is used, the stop plug is moved to the middle section of the elastic filament and secured such that the stripping filament is hidden in the stripping edge and can not continue retracting into the hollow cannula.

Furthermore, the material for said memory elastic filament is nonmetal and/or metal alloy.

Furthermore, the hollow cannula has a diameter of 1-4 mm, the elastic filament has a diameter of 0.3-0.6 mm, and the stripping edge has a length of 1-5 mm.

Preferably, the hollow cannula has a diameter of 2-3 mm, the elastic filament has a diameter of 0.3-0.46 mm, and the stripping edge has a width of 3-4 mm.

Another object of the present invention is to provide a kit of cannulas with memory elastic filament, consisting of a number of sets of cannulas with memory elastic filament with different models and different sizes.

Further, the elastic filaments in the kit have a diameter of 0.3048 mm (0.012 inch), 0.3556 mm (0.014 inch), 0.4064 mm (0.016 inch) etc., respectively.

In the present invention, the primary stripping structure may strip away the maxillary sinus floor mucous alone, but the secondary stripping structure needs the help of the primary stripping structure to strip away the sinus mucous.

The present invention may strip away the maxillary sinus floor mucous broadly and facilitate lifting the bone height.

In the animal experiment of sheep and the clinical experiment, the stripping length obtained at a flat sinus floor is 23.03±4.92 mm, and the stripping length at sinus floor with a slope of 60°~90° is 19.00±5.06 mm.

The present invention has advantages in the following aspects:

1. The present invention has a larger stripping range of mucous than traditional single stripper.
2. The secondary stripping structure adopting an ultra-elastic and/or memory elastic filament is used as a dulledge to stripping away mucous membrane for with a sound effect.
3. During implementation, the present invention has a secondary stripping structure (primary stripping structure and secondary stripping structure) and can accomplish five operations:
    (1) stripping away the sinus floor mucous membrane priliminarily with the primary stripping structure;
    (2) using the secondary stripping structure to allow the stripping filament to extend out of the stripping edge, thereby further stripping away the sinus floor mucous membrane;
    (3) rotating the hollow cannula horizontally to rotate the stripping filament horizontally, stripping away mucous around the position of accessing plane;
    (4) securing the hollow cannula and rotating the elastic filament or stop plug horizontally to reverse (turn around) the stripping filament, stripping away mucous membrane on a steep rising bone wall;
    (5) securing the hollow cannula with elastic filament or stop plug on both ends remaining in different motions to change the shape of stripping filament, stripping away the mucous membrane.
4. The memory elastic filament cannula equipment provided in the present invention is simple and small.
5. The present invention provides a kit of memory elastic filament cannulas, in which hollow cannulas of different models may be selected according to the diameter of the implant hole, elastic filaments with different diameters may be selected according to resilience of the mucosa, which has elasticity, strength and gental force, may effectively reduce the probability of sinus mucosa perforation, facilitating practical clinical operation.

The elastic filament mentioned in the present invention refers to a substance with ultra-elasticity and/or memory characteristics synthesized by a certain method with nonmetal or two or more metal and metal (or nonmetals).

Ultra-elasticity refers to a phenomenon in which a material has an elasticity potential function that is a scalar function of the strain tensor, the derivative of its corresponding strain component is the corresponding stress component and the strain may restore automatically while offloaded.

The stress and strain are no longer in a linear corresponding relationship, but correspond to each other in the form of elastic energy function.

Memory refers to the performance of a material that can restore after deformation.

The shape of the end of the elastic filament mentioned in the present invention is not limited to circle but may be various shapes such as ellipse, quadrilateral and polygon.

The stripping edge refers to the part of the primary stripping structure that is located at the top of the hollow canulla which may control the elastic filament to extend downward and forward from the end of the hollow canulla.

The stripping edge is preferably of an arc shape.

The present invention utilizes the ultra-elasticity and/or memory of the elastic filament. Upon the beginning of the product manufacturing, the elastic filament (especially, it is end) is processed to have a shape suitable for stripping away the sinus floor mucosa. During the product assembly, the elastic filament is placed into the hollow canulla. And while in use, the stripping filament still maintains the shape suitable for stripping the sinus floor mucosa.

Furthermore, the cannula with memory elastic filament while used needs the ultra-elasticity and/or memory of the elastic filament to adapt to various complex stripping conditions.

Figure 1:
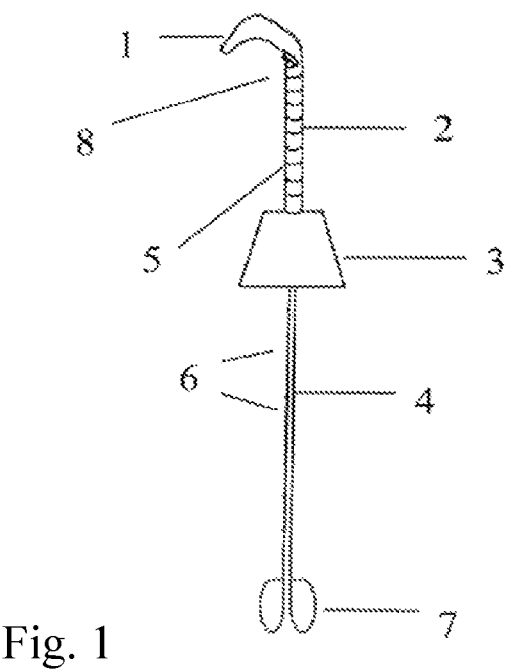
FIG. 1 is a structure diagram of a cannula with memory elastic filament.
Figure 2:
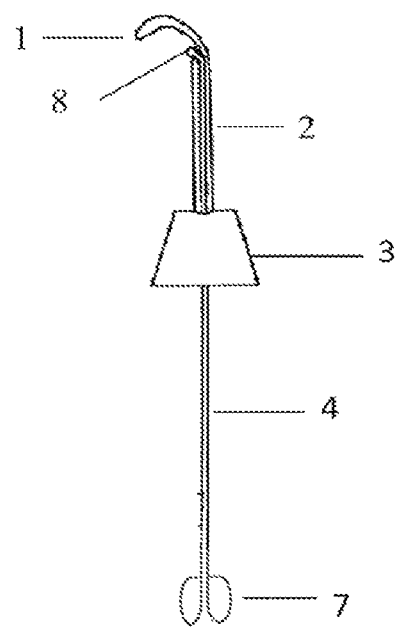
FIG. 2 is a cross-section view of the middle portion of the cannula with memory elastic filament.
Figure 3:
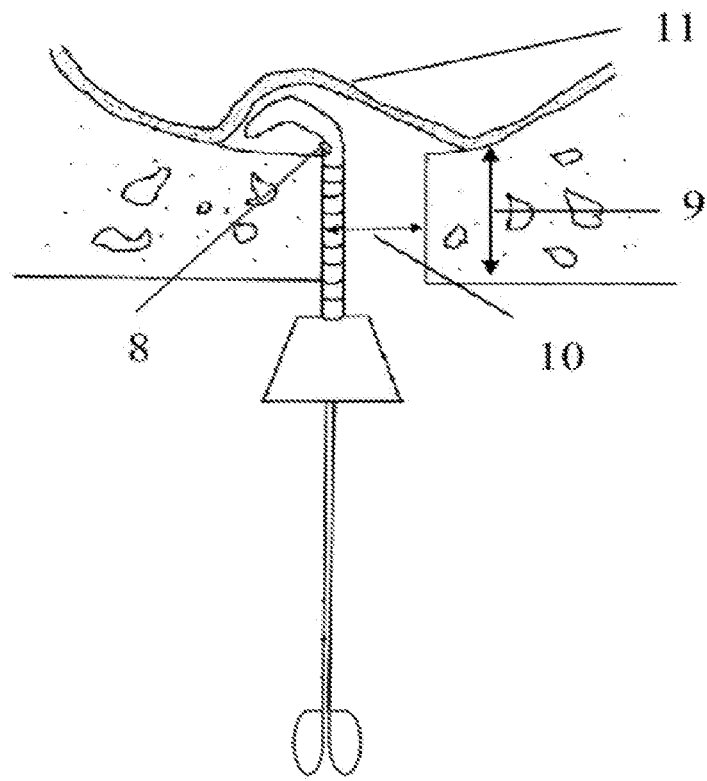
FIG. 3 is a diagram of stripping away mucosa with the cannula with memory elastic filament.
Figure 4:
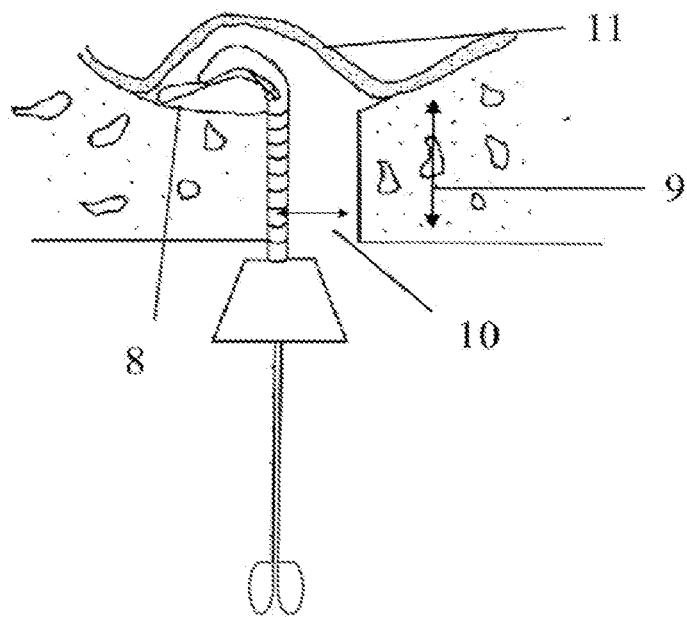
FIG. 4 is a diagram of stripping away mucosa with the cannula with memory elastic filament.

In the figures, 1. stripping edge; 2. Hollow cannula; 3. Holding end; 4. Elastic filament; 5. Annular scale; 6. Scale; 7. Stop plug; 8. stripping filament; 9. The height of alveolar bone; 10. Bone hole; 11. maxillary sinus mucous

DETAILED DESCRIPTION

The present invention will be further described below with respect to specific embodiments which only serves to explain the present invention rather than being construed to limit the present invention. Those of ordinary skill in the art may understand that these embodiments may be subject to various changes, modifications, substitutions and variations without departing from the principle and spirit of the present invention and the scope of the present invention is only defined by the claims and equivalents thereof.

Embodiment 1

Stripping away the maxillary sinus floor mucous with the primary stripping structure: placing the hollow cannula 2 into the bone hole 10 slowly, holding the hollow cannula 2 or the holding end 3 to strip away mucous with the stripping edge, slowly rotating the hollow cannula 2 horizontally to strip away the maxillary sinus floor mucous 11 by one round, thereby obtaining a stripping range of about 3 mm around the hole.

Embodiment 2

Stripping away the maxillary sinus floor mucous with the secondary stripping structure: placing the hollow cannula 2 into the bone hole 10 slowly (now the stripping filament 8 is hidden in/under the stripping edge 1), and operating the elastic filament 4 or the stop plug 7 to allow the stripping filament 8 extend downward and forward along the stripping edge 1. Suitable stripping length may be selected according to the required lifting height.

Embodiment 3

Stripping away the maxillary sinus floor mucous with the secondary stripping structure: placing the hollow cannula 2 into the bone hole 10 slowly (now the stripping filament 8 is hidden in/under the stripping edge 1), and operating the elastic filament 4 or the stop plug 7 to allow the stripping filament 8 extend downward and forward along the stripping edge 1. Then, rotating the hollow cannula 2 or the holding end 3 horizontally and drive the stripping filament 8 to rotate with the hole midpoint as a center, which may strip away mucous around the hole in a large range.

Embodiment 4

Stripping away the maxillary sinus floor mucous with the secondary stripping structure: placing the hollow cannula 2 into the bone hole 10 slowly (now the stripping filament 8 is hidden in/under the stripping edge 1), and operating the elastic filament 4 or the stop plug 7 to allow the stripping filament 8 extend downward and forward along the stripping edge 1. In a condition that there is a steep rising bone wall away from the hole, since the stripping edge 1 restricts the stripping filament 8 to only extend forward and downward and block the stripping filament 8 from extending further forward, it is now possible to secure the hollow cannula 2 or the holding end 3 and rotate the elastic filament 4 or the stop plug 7 such that the stripping filament 8 reverses with the stripping edge 1 as the center and in turn strip away the maxillary sinus mucous 11 proximate to the steep rising and further crawl farther.

Embodiment 5

Stripping away the maxillary sinus floor mucous with the secondary stripping structure: placing the hollow cannula 2 into the bone hole 10 slowly (now the stripping filament 8 is hidden in/under the stripping edge 1), and operating the elastic filament 4 or the stop plug 7 to allow the stripping filament 8 extend downward and forward along the stripping edge 1. Secure the hollow cannula 2 and allow the two stop plugs 7 to keep different motions such that the stripping filament 8 changes its shape for stripping away mucous with stripping filament 8 with different shapes. Alternatively, secure one end of the elastic filament 4 or the stop plug 7 and draw the other end of the elastic filament 4 or the stop plug 7 such that the stripping filament 8 changes its shape for stripping away mucous with stripping filament 8 with different shapes.

The invention claimed is:

1. A cannula with memory elastic filament for stripping away sinus mucosa, comprising:
    a primary stripping structure: and
    a secondary stripping structure,
    wherein said primary stripping structure comprises a hollow cannula and a stripping edge, the stripping edge connected on and fixed to a top of the hollow cannula,
    wherein said secondary stripping structure comprises an elastic filament,
    wherein, said elastic filament is made of a shape memory material with elasticity,
    wherein said elastic filament is folded into double strands and positioned in said hollow cannula, an upper end of said elastic filament extends out from the top of said hollow cannula, and two strands of a lower end of said elastic filament extend out of a bottom of said hollow cannula,
    wherein the two strands of the lower end of said elastic filament are separated with each other and can be controlled separately,
    wherein the shape of said stripping edge is an arc and the elastic filament is bent downward by said stripping edge when the elastic filament extends out of the hollow cannula, and
    wherein the upper end of said elastic filament that extends beyond said hollow cannula is variable in size, extension direction and shape by adjusting the two strands of the lower end of said elastic filament.

2. The cannula with memory elastic filament of claim 1, wherein the elastic filament is machined to have a shape suitable for stripping away mucosa from the maxillary sinus floor.

3. The cannula with memory elastic filament of claim 1, wherein the upper end of said elastic filament that extends beyond the hollow cannula is of irregular circle shape.

4. The cannula with memory elastic filament of claim 1, wherein the upper end of the elastic filament is controlled to be hidden under the stripping edge.

5. The cannula with memory elastic filament of claim 1, wherein one end of said hollow cannula has a holding part and has a stop plug; and
    wherein the hollow cannula or the elastic filament is marked with a scale.

6. The cannula with memory elastic filament of claim 1, wherein the elastic filament is made of a nonmetal or a metal alloy.

7. The cannula with memory elastic filament of claim 1, wherein the hollow cannula has a diameter of 1-4 mm, the elastic filament has a diameter of 0.3-0.6 mm, and the stripping edge has a length of 1-5 mm.

\* \* \* \* \*